United States Patent
Tesar

(10) Patent No.: US 6,649,030 B1
(45) Date of Patent: Nov. 18, 2003

(54) PHYSICAL VAPOR DEPOSITION OF RADIOPAQUE MARKINGS ON A GRAFT

(75) Inventor: Aleta A Tesar, Livermore, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/652,945

(22) Filed: Aug. 31, 2000

(51) Int. Cl.⁷ .......................... C23C 14/34; C23C 16/00
(52) U.S. Cl. ............................ 204/192.14; 204/192.15; 427/2.1; 427/2.24; 427/2.25; 427/468; 427/250; 427/251
(58) Field of Search ................. 204/192.14, 192.15; 427/2.1, 2.24, 2.25, 468, 250, 251

(56) References Cited

U.S. PATENT DOCUMENTS

| | | | |
|---|---|---|---|
| 4,202,349 A | 5/1980 | Jones | 600/502 |
| 4,311,573 A | 1/1982 | Mayham et al. | 522/129 |
| 4,589,964 A | 5/1986 | Mayham et al. | 522/85 |
| 4,693,237 A | 9/1987 | Hoffman et al. | 128/899 |
| 4,716,900 A | 1/1988 | Ravo et al. | 606/110 |
| 4,719,916 A | 1/1988 | Ravo et al. | 606/156 |
| 4,787,391 A | 11/1988 | Elefteriades | 600/431 |
| 4,905,693 A | 3/1990 | Ravo | 606/153 |
| 4,909,258 A | 3/1990 | Kuntz et al. | 600/435 |
| 5,104,399 A | 4/1992 | Lazarus | 623/1.14 |
| 5,144,959 A | 9/1992 | Gambale et al. | |
| 5,151,105 A | 9/1992 | Kwan-Gett | 623/1.32 |
| 5,234,435 A | 8/1993 | Seagrave, Jr. | 606/103 |
| 5,275,622 A | 1/1994 | Lazarus et al. | 623/1.11 |
| 5,370,691 A | 12/1994 | Samson | 623/1.22 |
| 5,375,603 A | 12/1994 | Feiler | 600/474 |
| 5,387,247 A * | 2/1995 | Vallana et al. | 623/66 |
| 5,397,345 A | 3/1995 | Lazarus | 128/898 |
| 5,415,664 A | 5/1995 | Pinchuk | 623/1.11 |
| 5,419,324 A | 5/1995 | Dillow | 600/426 |
| 5,419,774 A | 5/1995 | Willard et al. | 604/22 |
| 5,456,694 A | 10/1995 | Marin et al. | 623/1.11 |
| 5,489,295 A | 2/1996 | Piplani et al. | 623/1.35 |
| 5,507,769 A | 4/1996 | Marin et al. | 606/198 |
| 5,549,679 A | 8/1996 | Kuslich | 623/17.12 |
| 5,556,414 A | 9/1996 | Turi | 623/1.11 |
| 5,558,652 A | 9/1996 | Henke | |
| 5,562,728 A | 10/1996 | Lazarus et al. | 623/1.14 |

(List continued on next page.)

OTHER PUBLICATIONS

John A. Thornton, "Metallurgical And Protective Coatings: High Rate Sputtering Techniques", Thin Solid Films, 80 (1981) pp. 1–11. Printed in The Netherlands.

Donald M. Mattox, "Handbook of Physical Vapor Deposition (PVD) Processing: Film Formation, Adhesion, Surface Preparation adn Contamination Control", Society of Vacuum Coaters, Albuquerque, New Mexico, Noyes Publications, Westwood, New Jersey, USA. pp. 324–327, 1998.

Airco Temescal (A division of Airco, Inc.), "Physical Vapor Deposition" USA pp. 90–97, 1976.

Talivaldis Spalvins, "Sputtering And ION Plating: Characteristics of ION Plated Films Including Mechanical Properties and Lubrication", Technology Utilization Office 1972, National Aeronautics And Space Administration, Washington, D.C., pp. 41–57.

*Primary Examiner*—Rodney G. McDonald
(74) *Attorney, Agent, or Firm*—Blakely, Sokoloff, Taylor & Zafman LLP

(57) ABSTRACT

Physical vapor deposition of radiopaque markings onto a graft is described. A graft is placed into a chamber, and a radiopaque material is vaporized and then deposited onto the graft. The chamber is kept at a temperature below the damage threshold of the graft material. A template optionally placed on the graft may define the design of the deposited radiopaque markings. The deposited radiopaque markings of the present invention may have any design and may comprise any radiopaque material.

34 Claims, 3 Drawing Sheets

U.S. PATENT DOCUMENTS

| | | | |
|---|---|---|---|
| 5,591,195 A | 1/1997 | Taheri et al. ............... 623/1.11 |
| 5,607,442 A | 3/1997 | Fischell et al. |
| 5,609,625 A | 3/1997 | Piplani et al. ............... 128/898 |
| 5,628,783 A | 5/1997 | Quiachon et al. |
| 5,628,788 A | 5/1997 | Pinchuk ...................... 623/1.2 |
| 5,639,278 A | 6/1997 | Dereume et al. .......... 623/1.13 |
| 5,662,700 A | 9/1997 | Lazarus et al. ............. 606/194 |
| 5,667,523 A | 9/1997 | Bynon et al. ............... 623/1.13 |
| 5,669,936 A | 9/1997 | Lazarus ...................... 623/1.23 |
| 5,676,697 A | 10/1997 | McDonald ................. 623/1.35 |
| 5,679,470 A | 10/1997 | Mayer |
| 5,681,336 A | 10/1997 | Clement et al. ............. 606/159 |
| 5,693,083 A | 12/1997 | Baker et al. ............... 623/1.11 |
| 5,695,517 A | 12/1997 | Marin et al. ............... 623/1.13 |
| 5,697,970 A | 12/1997 | Schmitt et al. ............. 623/1.51 |
| 5,713,917 A | 2/1998 | Leonhardt et al. .......... 606/194 |
| 5,718,159 A | 2/1998 | Thompson ...................... 87/33 |
| 5,720,776 A | 2/1998 | Chuter et al. .............. 623/1.36 |
| 5,725,572 A | 3/1998 | Lam et al. |
| 5,728,042 A | 3/1998 | Schwager ................... 623/1.15 |
| 5,728,150 A | 3/1998 | McDonald et al. ............. 600/3 |
| 5,733,325 A | 3/1998 | Robinson et al. ............ 623/1.11 |
| 5,747,128 A | 5/1998 | Campbell et al. .......... 428/35.7 |
| 5,749,920 A | 5/1998 | Quiachon et al. .......... 623/1.23 |
| 5,758,562 A | 6/1998 | Thompson ...................... 87/33 |
| 5,769,885 A | 6/1998 | Quiachon et al. ........... 128/898 |
| 5,782,907 A | 7/1998 | Frantzen et al. ............ 606/194 |
| 5,782,909 A | 7/1998 | Quiachon et al. ........... 606/194 |
| 5,800,518 A | 9/1998 | Piplani et al. ............... 128/898 |
| 5,800,522 A | 9/1998 | Campbell et al. ........... 128/898 |
| 5,824,039 A | 10/1998 | Piplani et al. ............. 622/1.11 |
| 5,824,047 A | 10/1998 | Moreland .................. 623/1.11 |
| 5,824,055 A | 10/1998 | Spiridigliozzi et al. .... 623/1.11 |
| 5,827,310 A | 10/1998 | Marin et al. ................. 606/167 |
| 5,843,164 A | 12/1998 | Frantzen et al. ............ 623/1.16 |
| 5,843,167 A | 12/1998 | Dwyer et al. ............... 623/1.14 |
| 5,843,171 A | 12/1998 | Campbell et al. ........... 606/198 |
| 5,858,556 A | 1/1999 | Eckert et al. |
| 5,873,906 A | 2/1999 | Lau et al. .................... 128/898 |
| 5,875,782 A | 3/1999 | Ferrari et al. ............... 128/898 |
| 5,876,783 A | 3/1999 | Dobson |
| 5,891,193 A | 4/1999 | Robinson et al. ........... 128/898 |
| 5,893,859 A | 4/1999 | Marin et al. ................. 606/159 |
| 5,902,334 A | 5/1999 | Dwyer et al. ............... 606/194 |
| 5,906,641 A | 5/1999 | Thompson et al. ........ 623/1.15 |
| 5,919,126 A | 7/1999 | Armini |
| 5,919,225 A | 7/1999 | Lau et al. .................... 606/198 |
| 5,934,284 A | 8/1999 | Plaia et al. .................. 128/898 |
| 5,935,161 A | 8/1999 | Robinson et al. ........... 128/898 |
| 5,944,750 A | 8/1999 | Tanner et al. ............... 623/1.23 |
| 5,957,940 A | 9/1999 | Tanner et al. ............... 606/155 |
| 5,957,973 A | 9/1999 | Quiachon et al. ........... 623/1.23 |
| 5,957,974 A | 9/1999 | Thompson et al. ........ 623/1.13 |
| 6,057,414 A * | 5/2000 | Razavi ....................... 527/491 |
| 6,174,329 B1 * | 1/2001 | Callol et al. ................. 623/1.34 |

\* cited by examiner

PHYSICAL VAPOR DEPOSITION OF RADIOPAQUE MARKINGS ON A GRAFT

FIELD OF THE INVENTION

The present invention relates to radiopaque markers and, more specifically, radiopaque markings that are physical vapor deposited onto graft material.

BACKGROUND

Prosthetic grafts are used to repair diseased or damaged vessels as well as to help maintain the patency of body lumens. One way of implanting a prosthetic graft within a body lumen involves open surgical repair of a damaged or diseased vessel. For example, open surgical repair of an abdominal aortic aneurysm (AAA) requires a large incision to be made through the abdominal wall. The patient's internal organs are moved aside to provide the surgeon access to the aorta. The aorta is then cut, and the prosthetic graft is placed at the site of the aneurysm.

Open surgical repair of AAA and implantation of the prosthetic graft into patients who need such treatment is not always the preferred procedure. Many patients who suffer from AAA also suffer from other ailments and cannot endure such a highly invasive surgical procedure. Those who do undergo such an open surgical procedure typically need to stay in the hospital for several days and require several months of convalescence to fully recuperate.

Less invasive alternatives to open surgical implantation of a prosthetic graft exist. One example is a minimally invasive endovascular treatment of AAA using a catheter delivery system, such as the ANCURE® System developed and manufactured by Guidant Corporation. The use of the ANCURE® System requires making an incision to a femoral artery. A surgeon inserts the delivery catheter, which contains a compressed prosthetic graft, through the femoral artery and navigates the catheter through the patient's vasculature to deliver the prosthetic graft to the site of the aneurysm, where the graft is implanted. The catheter is then removed. Similar endovascular procedures are used to implant prosthetic grafts in other body lumens.

One difficulty associated with endovascular procedures is navigating the delivery catheter through the patient's vasculature. Vascular anatomy can be quite tortuous and narrow. The outer diameter (i.e., containing the profile) of the catheter graft is thus an important feature. There exists a general need to minimize the bulk of the graft in order to minimize the profile of the catheter.

In performing such endovascular procedures, a physician typically will use a fluoroscope to help navigate the catheter through the vasculature. The catheter typically will have several radiopaque markers thereon, particularly near the distal end where the graft is carried, so that the physician can see various points along the catheter under the fluoroscope. The graft itself typically has several radiopaque markers to assist the physician in positioning and orienting the graft within the vessel. The radiopaque markers on the graft also help the physician visualize the graft after implantation, to make sure that the graft remains in its proper place and has not collapsed or twisted or otherwise deformed.

Graft radiopaque markers generally are wires or coils made of a radiopaque metal or alloy, such as platinum, platinum-tungsten, or platinum-iridium, which are woven into or sewn onto the graft material. Alternatively, polymeric fibers coated or filled with radiopaque particles are sometimes woven into the graft material. Typically the weaving or sewing of such radiopaque markers onto the graft material is done by hand, a very time consuming and labor intensive procedure requiring highly skilled laborers. Radiopaque coils and wires also add undesirable bulk to the graft.

Physical vapor deposition (PVD) processes have been used to plate or deposit thin layers of metal onto metallic or semiconductor substrates. Metal layers on the order of a few microns or less can be formed using PVD processes such as vacuum evaporation and sputter deposition, and such processes can be readily scaled for large throughput manufacturing.

The primary difficulty in applying PVD to form radiopaque markings onto a graft is that typical PVD conditions may damage the graft material, making the graft material unsuitable for use as a graft. Vaporization of the radiopaque material requires high energy to be applied to the source, and material vaporized from the source would tend to transfer this energy to the graft material, which may cause localized melting or burning of the graft material where the vaporized material is deposited. Ionization of the radiopaque material, which may occur during vaporization, tends to generate ultraviolet radiation, which also may damage the graft material.

Given the high energies and generally harsh processing conditions under which physical vapor deposition occurs, PVD processes have not heretofore been considered for use with graft materials.

SUMMARY OF THE INVENTION

Physical vapor deposition of a radiopaque marking onto a graft is described. In one aspect, a method for physical vapor depositing a radiopaque marking onto a graft is provided. A graft is placed in a chamber that has therein a source of a radiopaque material. The chamber is evacuated, and the radiopaque material is vaporized from the source in the chamber. The vaporized material is deposited onto the graft to form a radiopaque marking. Another aspect of the present invention provides a graft having a physical vapor deposited radiopaque marking.

BRIEF DESCRIPTION OF THE DRAWINGS

The present invention is illustrated by way of example, and not by way of limitation, in the figures in which.

DETAILED DESCRIPTION

A graft having a physical vapor deposited radiopaque marking and a method for forming the same are described herein. The present invention will be described below in connection with the Figures and with certain embodiments. In the following description, specific details are set forth to provide a thorough understanding of the present invention, however, those of ordinary skill in the art will appreciate that the present invention may be practiced without these specific details. In other instances, details of well-known steps, structures and techniques have been omitted to avoid obscuring the present invention.

In accordance with the present invention, a radiopaque marking is formed on a graft via physical vapor deposition (PVD). The present inventor has demonstrated that PVD processes such as vacuum evaporation, sputter deposition and the like may be successfully applied to form radiopaque markings on a graft.

As used herein, the term "vaporizing" (and related words) includes evaporating, sputtering, and other processes by which a solid or liquid material is transformed into a gaseous state. The term "radiopaque material" means any metal, alloy, or compound that is visible under a fluoroscope, and includes platinum, platinum-iridium, platinum-tungsten, tungsten and gold. It should be noted that radiopaque materials other than those listed above also may be used in accordance with the present invention.

Figure 1:
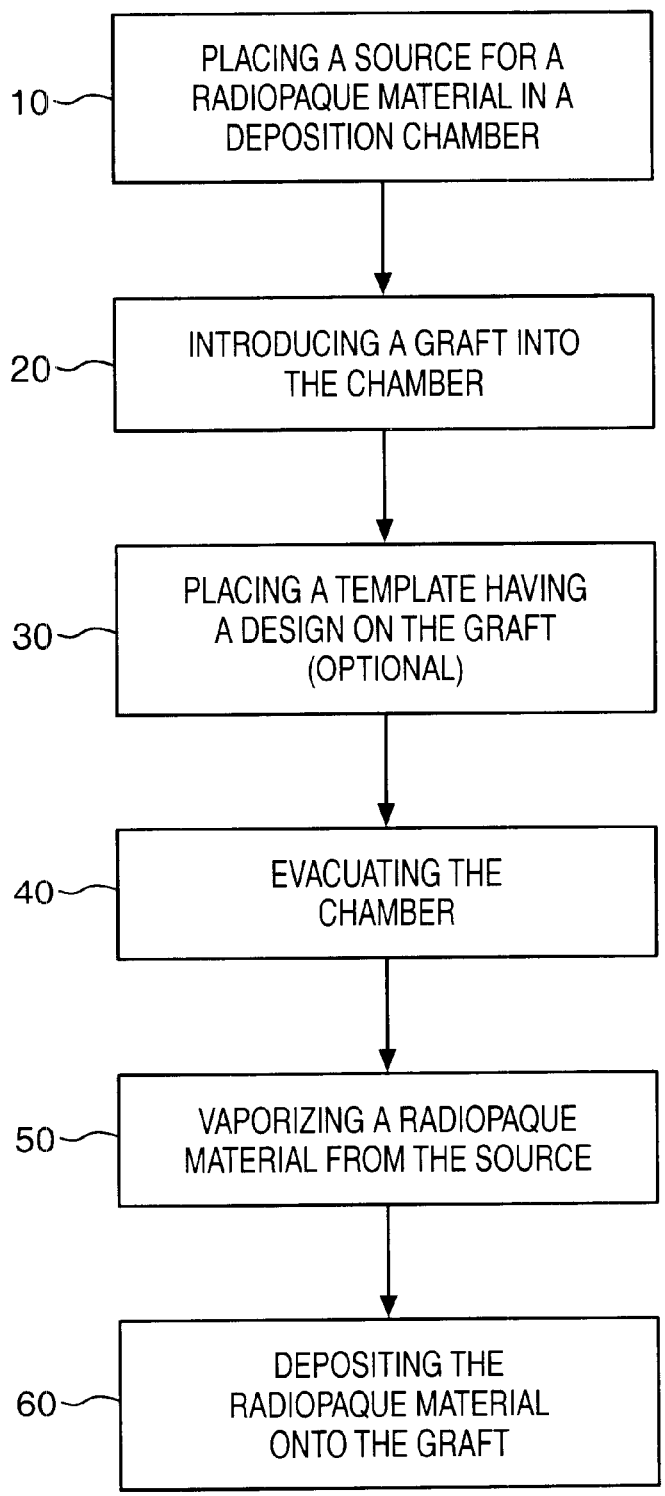
FIG. 1 is a flowchart illustrating one embodiment of a process of physical vapor depositing a radiopaque marking on a graft in accordance with one aspect of the present invention.

FIG. 1 outlines a method for physical vapor depositing a radiopaque marking on a graft in accordance with the present invention. Physical vapor deposition typically occurs within a deposition chamber. In a first step 10, a source for a radiopaque material is placed within the deposition chamber. The graft is placed into the chamber in a step 20. In an optional step 30, a template having a design therethrough is placed in contact with the graft. Next in step 40, the chamber is evacuated, and the radiopaque material is vaporized from the source in step 50. The radiopaque material may be vaporized using one of various PVD techniques, such as evaporation, sputtering, and the like. The vaporized material is deposited on the graft to form a radiopaque marking on the graft in step 60. Additionally, the graft may be rotated or moved through the vaporized material as it is being deposited to achieve a more uniform thickness of the radiopaque marking.

Where a template has been placed in contact with the graft, the vaporized material is deposited through the design of the template onto the graft, so that the radiopaque marking is formed on the graft in the shape of the design. Under some circumstances, where the radiopaque marking is not to have a defined design, a template is not used, and the vaporized material is deposited directly onto the graft. Use of a template may impart other advantages to the processes of the present invention, as will be discussed below.

The graft typically is made of a biocompatible polymer material, such as a polyethylene terephthalate (PET), a polyester, a polytetrafluoroethylene (PTFE), and the like. Other biocompatible materials also may be used within the scope of the present invention. In one embodiment, the graft is made of a textile or a fabric of the biocompatible material. Textiles or fabrics, such as woven materials, generally are used with the processes of the current invention because the vaporized material can conform to the texture of the textile or fabric, enhancing the adhesion of the physical vapor deposited radiopaque marking on the graft. In one embodiment, the graft is made of a woven PET fabric. The graft typically has a tubular shape and can have one or more bifurcations.

To prevent or reduce damage to the graft, the deposition typically occurs at a temperature below a damage threshold for the graft material. A damage threshold is a temperature at which a material loses the mechanical properties (e.g., flexibility, elasticity, etc.) that make the material useful for a graft. The damage threshold will vary depending on the graft material, and can be determined through well-known methods and without undue experimentation by those of ordinary skill in the art. For example, polyethylene terephthalate (PET) has a damage threshold of about 150° C. In one embodiment in which a radiopaque marking is deposited onto a graft comprising PET, the vacuum chamber is kept at a temperature of about 150° C. or less throughout the process according to the present invention.

The radiopaque material may be deposited at an average deposition rate in a range of about 0.1 nm per second to about 5 nm per second. In one embodiment, the initial deposition is done at a relatively low vaporization energy and relatively slow deposition rate, e.g., of about 0.1 nm per second. In another embodiment, the average initial deposition occurs in a range between about 0.1 nm per second to about 0.3 nm per second. The relatively slow deposition of the initial few tenths of a micron layer of radiopaque material permits heat to dissipate from the graft, minimizing localized heating of the graft material. Also, a relatively slow initial deposition enhances adhesion of the vaporized material to the graft. Once an initial layer of a few tenths of a micron is deposited on the graft, the deposition rate may be increased. The initial layer of radiopaque material helps shield the graft material from any ultraviolet radiation generated during vaporization and thus helps reduce the risk of damage to the graft material as the vaporization energy and the deposition rate are increased. In one embodiment, after the initial layer of radiopaque material is deposited on the graft, the (average) deposition rate is increased to about 0.3 nm per second.

Each radiopaque material has a different radiopacity, and the amount of radiopaque material to be deposited will depend upon the specific choice of radiopaque material. In general, it is desirable to have the vaporized material deposited to a thickness that will make the physical vapor deposited radiopaque marking clearly visible under a fluoroscope. In one embodiment, the vaporized material is deposited in varying thicknesses to form radiopaque markings having varying visibility, or opacity, under a fluoroscope. Typically, the vaporized material is deposited to form a radiopaque marking having a thickness in a range of about 0.5 $\mu$m to about 1 mm. In one embodiment in which the radiopaque material is platinum, the radiopaque marking is deposited to a thickness in a range of about 1 $\mu$m to about 10 $\mu$m.

Figure 2:
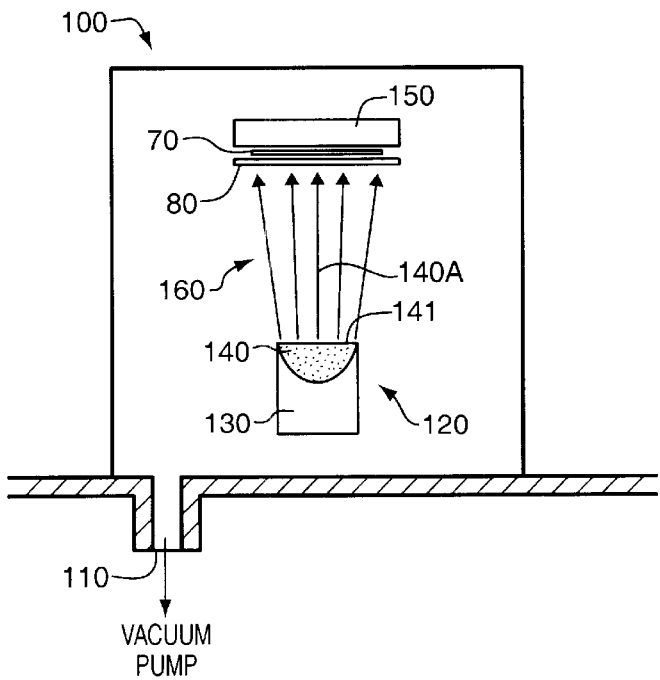
FIG. 2 shows an apparatus for implementing one embodiment of a process according to the present invention.

FIG. 2 depicts a vacuum evaporation apparatus for implementing one embodiment of a process of the present invention. A deposition chamber 100 is provided having an outlet 110 leading to a vacuum pump (not shown) to evacuate the chamber 100 which has therein a source 120, shown in this embodiment as a crucible or boat 130 holding a radiopaque material 140, and a base plate 150 facing opposite the source 120. A graft 70 is placed into the chamber 100 in contact with the base plate 150, and a template 80 is placed in contact with the graft 70 such that the graft is sandwiched between the base plate 150 and the template 80. As discussed above, use of a template is optional in the processes of the present invention, though a template generally is used to define a design of the radiopaque marking formed on the graft.

The radiopaque material 140 is evaporated from the source 120 using one of a variety of techniques, such as resistance heating, inductance heating, laser evaporation, electron beam heating, flash heating, and the like. The evaporated material travels from the surface 141 of the source 120 along straight-line paths 160 towards the base plate 150 and is deposited through the template 80 onto the graft 70 to form a radiopaque marking on the graft 70. In one embodiment, the graft 70 is rotated or moved through the vaporized material to achieve a more uniform deposition of the radiopaque marking.

The base plate 150 may be made of a conductive material, such as stainless steel, aluminum or the like. A conductive base plate would help conduct heat and any static charge away from the graft and thus help prevent or reduce damage to the graft. The graft, which typically has a tubular shape, may be placed flat against the base plate or slipped over the base plate. In FIG. 2, the base plate 150 is shown as having a substantially flat surface against which the graft is placed flat. In another embodiment, the base plate has a cylindrical shape generally conforming to the tubular shape of the graft, and the graft is fitted over the base plate like a sleeve. If the graft has one or more bifurcations, the base plate similarly could have one or more bifurcations to generally conform with the shape of the graft.

To shield the graft from any ultraviolet radiation generated by vaporization of the radiopaque material from the source, the graft may be positioned off-axis from the source. The vacuum evaporation apparatus shown in FIG. 2 has the graft 70 positioned facing opposite the source 120, substantially normal to the source axis 140A which is perpendicular to the surface 141 of the source 120. Thus, the graft in the embodiment shown in FIG. 2 directly faces any ultraviolet radiation generated at the surface 141 of the source 120 during vaporization. In another embodiment, the base plate may be placed off-axis from the source, such that the graft does not lie substantially normal to the source axis 140A. However, the angular distribution of evaporated particles from the source tends to be relatively small, so the graft typically is positioned substantially normal to the source axis 140A as shown in FIG. 2.

A template, if used, also can help shield the graft 70 from any ultraviolet radiation. If made of a conductive material, such as steel, aluminum, or the like, the template additionally may help conduct heat and static charge away from the graft and thus help prevent or reduce damage to the graft material. Because the template typically has a design cut therethrough, the graft will not be shielded where the design is cut. However, as the initial layer of vaporized material is deposited on the graft to form the radiopaque marking, the radiopaque marking itself can shield the graft material from any ultraviolet radiation.

In one embodiment, the template, if used, would sandwich the graft flat against the base plate, such as shown in FIG. 2. In another embodiment, where the base plate has a cylindrical shape and the graft is slipped over the base plate like a sleeve, the template may have a tubular shape similar to that of the graft, such that template fits over the graft like a sleeve. If the graft has one or more bifurcations, the template similarly could have one or more bifurcations conforming to the shape of the graft.

Figure 3A:
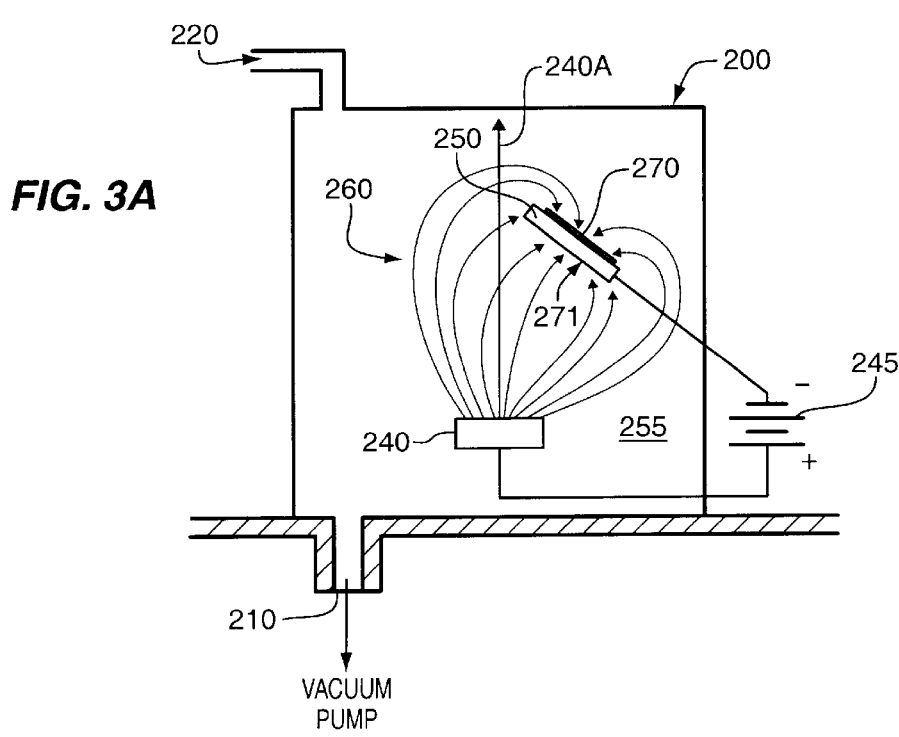
FIG. 3A shows one configuration of an apparatus for implementing another embodiment of a process according to the present invention.

FIG. 3A shows a sputter deposition apparatus according to another embodiment of the present invention. A chamber 200 is provided having an outlet 210 leading to a vacuum pump (not shown) for evacuating the chamber 200, and an inlet 220 for introducing a sputtering gas into the chamber 200. Argon or neon is typically used as the sputtering gas, though other gases may be used in accordance with the present invention. The vacuum chamber 200 further has therein a source 240 and a base plate 250 that are electrically connected through a power supply 245.

The base plate 250 in such sputter deposition embodiments typically is made of a conductive material, such as stainless steel, aluminum, or the like. The source 240 contains a radiopaque material and may be configured in one of various ways known in the art. For example, if the radiopaque material is a solid conductive material, e.g., a radiopaque metal such as platinum or gold, the source may be a disk or ingot of the radiopaque material. If, for example, the radiopaque material is a non-conductive material, the source may include a conductive (e.g., metal) cage or boat in which the radiopaque material is held. Other source configurations may be used in accordance with the present invention.

A graft 270 is placed into the chamber 200 in contact with the base plate 250. In one embodiment, the graft 270 is placed flat against the base plate 250. In another embodiment, the graft, which typically has a tubular shape, is slipped over the base plate. In cases where the graft has a generally tubular shape, the base plate may have a cylindrical shape generally conforming to the tubular shape of the graft, and the graft fitted over the base plate like a sleeve. If the graft has one or more bifurcations, the base plate similarly may have one or more bifurcations to generally conform with the shape of the graft.

In a sputter deposition process, the chamber 200 is evacuated and then backfilled with the sputtering gas. In one embodiment, an electric field is set up between the source 240, which acts as a cathode, and the base plate 250, which acts as an anode. The electric field causes electrons to accelerate and collide with the atoms or molecules of the sputtering gas. These collisions cause the atoms or molecules to ionize and generate secondary electrons, causing a plasma 255 to form in the chamber 200. The positively charged ions of the plasma 255 are accelerated towards the negatively charged source 240, causing ionized atoms or molecules or clusters of the radiopaque material to be ejected from the source 240. In other words, the positively charged ions of the plasma 255 sputter ionized atoms or molecules or clusters of the radiopaque material from the source 240. The ionized sputtered material travels along the electric field lines 260 between the source 240 and the base plate 250 to be deposited on the graft 270.

Figure 3B:
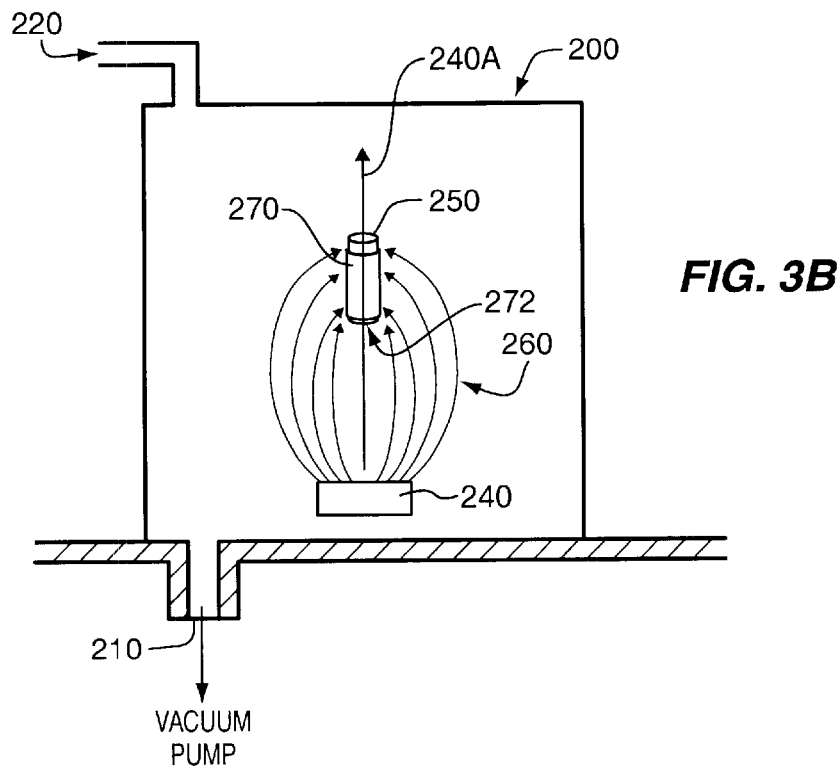
FIG. 3B shows another configuration of an apparatus for implementing still another embodiment of a process according to the present invention.

Because the sputtered material follows the electric field lines 260 towards all points on the anode, the radiopaque markings may be deposited on the entire surface of the graft 270 during the deposition process. Additionally, because the sputtered material follows the electric field lines 260 instead of travelling along straight-line paths (as the evaporated material in the embodiment shown in FIG. 2 does), the graft 270 may be placed further off-axis from the source axis 240A and thus be exposed less to the ultraviolet radiation generated at the source 240. Alternatively, as illustrated in FIG. 3B, the graft 270 may be positioned with an opening 272 of its tubular shape facing the source 240, such that none of the surface of the graft directly faces the source 240.

With the sputter deposition process, the graft may be further shielded from the ultraviolet radiation generated at the source by shielding the surface of the graft on the side 271 facing the source and depositing the sputtered material only on the sides not facing the source. The graft may then be rotated and the radiopaque material deposited on the previously shielded side while the other sides are now shielded.

A template, if used, also can help shield the graft 270 from any ultraviolet radiation. The template may be made of a conductive material, such as steel, aluminum, or the like, to help conduct heat and static charge away from the graft. A conductive template further may be electrically connected with the base plate and act in combination with the base plate as the anode.

The present invention envisions that a sputter deposition process such as described above may be modified or enhanced through techniques, such as with ion-beams, magnetron sources, lasers, etc.

The physical vapor deposited radiopaque marking may be formed in various shapes. The template acts as a mask during the deposition process, such that the design of the template defines the shape of the radiopaque marking on the graft. The design may be cut in the template using one of various techniques, such as laser cutting, etching, etc. Advantageously, the design will differentiate between different parts of the graft and can indicate whether the graft is properly positioned and oriented inside a patient's body when viewed with a fluoroscope.

Figure 4:
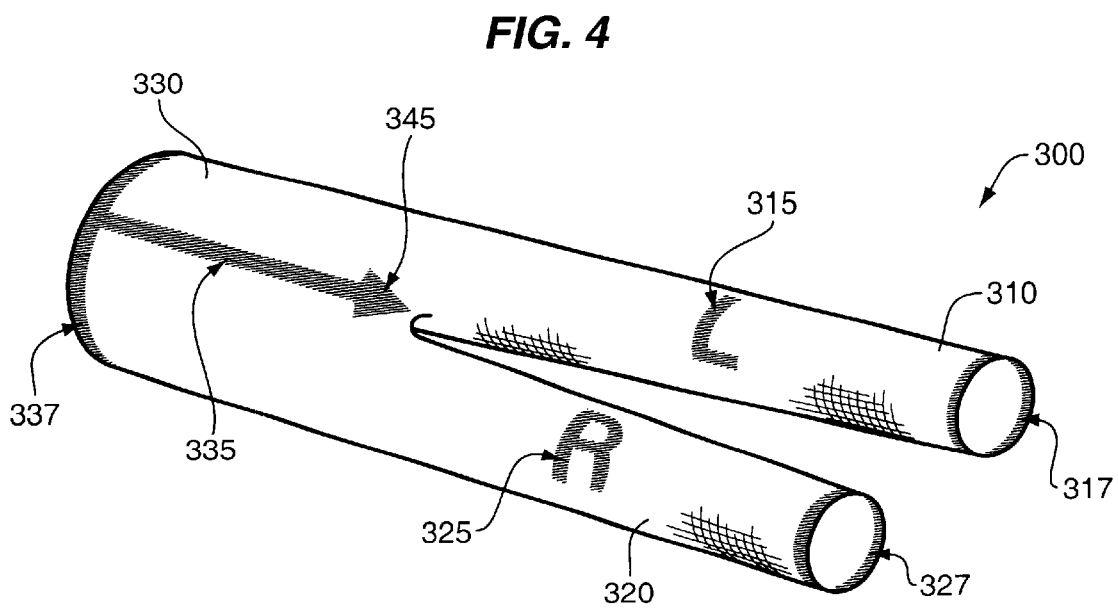
FIG. 4 shows one embodiment of a graft having radiopaque markings formed in accordance with the present invention.

For example, FIG. 4 shows an embodiment of a bifurcated graft 300 having various radiopaque markings thereon. In this embodiment, a left leg 310 having a radiopaque marking of a letter "L" 315 is differentiated from a right leg 320 having a radiopaque marking of a letter "R" 325. Each leg also has a radiopaque marking at the opening of each leg 317, 327 to visualize where each leg ends. The bifurcated graft 300 further comprises a main body 330 that has a radiopaque marking, in this embodiment a radiopaque line 335 and a radiopaque ring 337 surrounding the opening of the main body. The bifurcation is indicated by a radiopaque marking of an arrowhead 345. The radiopaque markings shown in FIG. 4 are only exemplary, and radiopaque markings having various other designs may be formed according to the present invention.

EXAMPLE

To demonstrate the feasibility of applying PVD to forming radiopaque markings on graft material, approximately 2 μm of palladium (Pd) was physical vapor deposited on a woven PET graft using a bench top argon (Ar) ion beam sputtering unit. In this example, a Sputter Coater® bench top Ar-ion beam sputtering unit available from Structure Probe, Inc. was used. The 4"-diameter chamber had therein a 2"-diameter Pd disk as the source. The woven PET graft was introduced into the chamber and placed in contact with the base plate. The base plate was made of aluminum and positioned on-axis about 1" from the Pd source. An aluminum template was placed directly on the graft facing the source and electrically connected with the base plate. The chamber was evacuated and then filled with Ar to a pressure of less than about 0.1 millibar. A current of about 20 milliamperes was applied between the Pd source and the base plate/template to vaporize the Pd. The current was cycled on and off to deposit an initial layer of about 0.5 μm of Pd at an average deposition rate of about 0.1 nm per second. An additional about 1.5 μm of Pd was deposited on the graft at an average rate of about 0.3 nm per second until a radiopaque marking having a thickness of about 2 μm of Pd was formed on the graft.

Those of ordinary skill in the art will recognize that the present invention is not limited to those PVD processes described above, and that various PVD techniques may be used to deposit radiopaque materials onto graft materials. Several other modifications, variations and improvements may be made to the embodiments described above and still fall within the scope of the invention as claimed below.

What is claimed is:

1. A method comprising:
    providing a deposition chamber containing a source of a radiopaque metal;
    introducing a graft comprising a polymeric material having a damage threshold into the chamber in contact with a conductive base plate;
    evacuating the chamber;
    vaporizing the radiopaque metal from the source to form a vaporized metal within the evacuated chamber;
    depositing the vaporized metal onto the graft to form a radiopaque marking that is visible under a fluoroscope while maintaining a temperature that is not greater than the damage threshold; and
    conducting heat from the graft into the conductive base plate.

2. The method as described in claim 1, wherein depositing comprises depositing an initial layer of the vaporized metal having a thickness that is at least 0.1 μm at an average initial rate in a range of about 0.1 nm to about 0.3 nm per second and then increasing the rate of deposition of the vaporized metal onto the graft.

3. The method as described in claim 1:
    wherein introducing the graft into the chamber comprises introducing the graft into the chamber such that a first portion of the graft that is facing the source is shielded in order to reduce exposure to ultraviolet radiation generated at the source;
    wherein depositing comprises depositing sputtered metal on a second portion of the graft that is not facing the source;
    the method further comprising, after depositing the sputtered metal on the second portion, rotating the graft so that the first portion of the graft is not facing the source; and
    wherein depositing further comprises depositing sputtered metal on the first portion of the graft after it has been rotated so that it is not facing the source.

4. The method as described in claim 1, wherein the graft comprises a tubular shaped portion and wherein said introducing includes positioning the graft relative to the source so that an opening faces the source.

5. The method as described in claim 1, wherein said introducing the graft into the chamber in contact with the conductive base plate comprises slipping the graft over the conductive base plate.

6. The method as described in claim 1:
    wherein the graft comprises a tubular shaped portion;
    wherein the conductive base plate has a cylindrical shaped portion that generally conforms to the tubular shaped portion of the graft; and
    wherein introducing the graft into the chamber in contact with the conductive base plate comprises slipping the tubular shaped portion of the graft over the cylindrically shaped portion of the base plate.

7. The method as described in claim 1:
    wherein the graft has a bifurcation and the conductive base plate has a conforming bifurcation; and
    wherein introducing the graft into the chamber in contact with the conductive base plate comprises slipping the bifurcation of the graft over the conforming bifurcation of the conductive base plate.

8. The method as described in claim 1, wherein depositing the vaporized metal onto the graft to form the radiopaque marking comprises depositing a metal that is selected from the group consisting of platinum, iridium, tungsten, gold, and any combination thereof onto the graft at a deposition rate that is in a range of about 0.1 nm to about 5 nm per second to form a radiopaque marking having a thickness in a range of about 0.5 µm to about 1 mm.

9. The method as described in claim 1, wherein depositing the vaporized metal onto the graft to form the radiopaque marking comprises depositing platinum onto the graft to form a radiopaque marking having a thickness in a range of about 1 µm to about 10 µm.

10. The method as described in claim 1, further comprising moving the graft through the vaporized metal while depositing the vaporized metal onto the graft.

11. The method as described in claim 1:
further comprising placing a template having a design formed therethrough in a position relative to the graft prior to evacuating the chamber; and
wherein depositing comprises depositing the vaporized metal through the design in the template onto the graft.

12. The method as described in claim 1:
wherein the graft comprises a bifurcated graft having a main body and a bifurcation that defines a first leg and a second leg;
further comprising placing a template having a design formed therethrough in a position relative to the graft prior to evacuating the chamber; and
wherein depositing comprises depositing the vaporized metal through the design in the template onto the graft to deposit a differentiating marking on the first leg of the graft to allow the first leg to be differentiated from the second leg of the graft.

13. The method as described in claim 1, wherein the graft comprises a polyethylene terephthalate and the chamber is kept at a temperature that is not greater than about 150° C.

14. The method as described in claim 1, wherein the conductive base plate comprises a material that is selected from the group consisting of stainless steel and aluminum.

15. The method as described in claim 1, wherein the graft is maintained at the temperature that is not greater than the damage threshold.

16. The method as described in claim 1, wherein the chamber is maintained at the temperature that is not greater than the damage threshold.

17. The method as described in claim 1, wherein depositing comprises depositing a portion of the vaporized metal at an initial rate of deposition and then depositing another portion at an increased rate of deposition.

18. The method as described in claim 1, wherein introducing comprises positioning the graft off-axis from the source.

19. The method as described in claim 1, wherein depositing comprises depositing vaporized platinum onto the graft to form the radiopaque marking having a thickness that is greater than 1 µm.

20. The method as described in claim 1, further comprising placing a template having a design therethrough in a position relative to the graft.

21. The method as described in claim 20, wherein the template comprises a conductive metal template, wherein said placing the template comprises placing the conductive metal template into contact with the graft, and wherein the method further comprises conducting heat from the graft into the template.

22. The method as described in claim 20, wherein placing the template in a position relative to the graft comprises fitting a tubular portion of the template over a tubular portion of the graft.

23. The method as described in claim 1, wherein depositing comprises forming a leg identification marking.

24. The method as described in claim 1, wherein depositing comprises forming an opening identification marking.

25. The method as described in claim 12, wherein the differentiating marking comprises a letter that is selected from the group consisting of a letter R and a letter L.

26. A method comprising:
providing a deposition chamber containing a source of a radiopaque metal and a conductive cylindrically shaped base plate;
placing a tubular shaped graft comprising a polymeric textile having a damage threshold into the chamber in contact with the cylindrically shaped base plate by slipping the tubular graft over the cylindrically shaped base plate;
placing a template having a design therethrough in a position relative to the graft;
evacuating the chamber;
vaporizing the radiopaque metal from the source to form a vaporized metal within the evacuated chamber;
depositing the vaporized metal through the design in the template onto the graft to form a radiopaque marking which is visible under a fluoroscope, wherein depositing includes depositing at an average deposition rate in a range of about 0.1 nm per second to about 5 nm per second, to form a radiopaque marking having a thickness in a range of about 0.5 µm to about 1 mm, while maintaining a temperature that is not greater than the damage threshold; and
conducting heat from the graft into the conductive base plate.

27. The method as described in claim 26, wherein depositing comprises depositing an initial layer of the vaporized metal having a thickness that is at least 0.1 µm at an average initial rate in a range of about 0.1 nm to about 0.3 nm per second and then increasing the rate of deposition of the vaporized metal onto the graft.

28. The method as described in claim 26:
wherein introducing the graft into the chamber comprises introducing the graft into the chamber such that a first portion of the graft that is facing the source is shielded in order to reduce exposure to ultraviolet radiaiation generated at the source;
wherein depositing comprises depositing sputtered metal on a second portion of the graft that is not facing the source;
the method further comprising, after depositing the sputtered metal on the second portion, rotating the graft so that the first portion of the graft is not facing the source; and
wherein depositing further comprises depositing sputtered metal on the first portion of the graft after it has been rotated so that it is not facing the source.

29. The method as described in claim 26, wherein the graft comprises a tubular shaped portion that is positioned relative to the source so that an opening faces the source.

30. The method as described in claim 26:
wherein placing the template in the position relative to the graft comprises placing a conductive template into contact with the graft; and
further comprising conducting heat from the graft into the conductive template.

31. The method as described in claim 26:
wherein the polymeric material comprises a polyethylene terephthalate and the damage threshold is about 150° C.; and wherein the radiopaque metal comprises platinum deposited while maintaining the temperature not greater than about 150° C. as a layer having a thickness in a range about 1 μm to about 10 μm.

32. The method as described in claim 26, further comprising moving the graft through the vaporized metal while depositing the vaporized metal onto the graft.

33. The method as described in claim 26:

wherein the graft has a bifurcation and the conductive base plate has a conforming bifurcation; and wherein introducing the graft into the chamber in contact with the conductive base plate comprises slipping the bifurcation of the graft over the conforming bifurcation of the conductive base plate.

34. The method as described in claim 26:

wherein the graft comprises a bifurcated graft having a main body and bifurcation that defines a first leg and a second leg; and further comprising placing a template having a design formed therethrough in a position relative to the graft prior to evacuating the chamber; and wherein depositing comprises depositing the vaporized metal through the design in the template onto the graft including:

depositing a differentiating marking on the first leg of the graft to allow the first leg to be differentiated from the second leg of the graft, depositing a first opening identification mark at an opening of the first leg to allow the opening of the first leg to be identified, depositing a second opening identification mark at an opening of a main body to allow the opening of the main body to be identified, and depositing a bifurcation identification mark at the bifurcation to allow the bifurcation to be identified.

* * * * *